United States Patent
Tunc

[19]

[11] Patent Number: 5,824,247
[45] Date of Patent: Oct. 20, 1998

[54] PROCESS FOR FORMING HIGH STRENGTH INTERNAL BONE FIXATION DEVICES

[75] Inventor: Deger C. Tunc, East Brunswick, N.J.

[73] Assignee: Howmedica, Inc.

[21] Appl. No.: 854,430

[22] Filed: May 12, 1997

Related U.S. Application Data

[62] Division of Ser. No. 661,285, Jun. 10, 1996.

[51] Int. Cl.⁶ .................................................. B29C 39/12
[52] U.S. Cl. .......................... 264/135; 264/255; 264/265; 264/274
[58] Field of Search ................................... 264/135, 255, 264/265, 274; 470/9

[56] References Cited

U.S. PATENT DOCUMENTS

| | | | |
|---|---|---|---|
| 4,539,981 | 9/1985 | Tunc | ..................................... 128/92 B |
| 5,057,257 | 10/1991 | Neitzke | ..................................... 264/138 |
| 5,470,334 | 11/1995 | Ross et al. | ..................................... 606/72 |

*Primary Examiner*—Jan H. Silbaugh
*Assistant Examiner*—Edmund H. Lee
*Attorney, Agent, or Firm*—Joseph J. Kaliko

[57] ABSTRACT

Processes are set forth for forming high strength thermoplastic polymer bone fixation devices used, for example, in orthopedic surgery, where "strength" is quantified in terms a given device's pullout strength, tensile modulus, shear strength and breaking torque strength. Products of the aforementioned process are contemplated by the invention as well, with both "bioabsorbable" devices, for example, screws which are absorbable in an animal body and do not need to be removed after the bone in which they are inserted has healed; and non-bioabsorbable devices being described.

17 Claims, 2 Drawing Sheets

PROCESS FOR FORMING HIGH STRENGTH INTERNAL BONE FIXATION DEVICES

This application is a division, of application Ser. No. 08/661,285 filed Jun. 10, 1996.

BACKGROUND OF THE INVENTION

1. Field of the Invention

The invention relates generally to processes for forming high strength bone fixation devices used in surgery and to products obtained from the aforementioned processes.

More particularly, the invention relates to processes for forming high strength thermoplastic polymer bone fixation devices (for example screws), where "strength" is quantified in terms a given device's pullout strength, tensile modulus, shear strength and breaking torque strength.

Bone fixation devices that are "bioabsorbable", i.e., devices such as screws which are absorbable in an animal body and do not need to be removed after the bone in which they are inserted has healed; and non-bioabsorbable bone fixation devices, are both contemplated by the invention.

2. Description of the Related Art

It is well known to use bioabsorbable thermoplastic polymer materials, such as polyesters; and non-bioabsorbable thermoplastic polymer materials, such as polyacrylics, in the manufacture of sutures and bone fixation devices, such as rods, pins and screws.

For example, U.S. Pat. Nos. 4,539,981 and 4,550,449 describe bioabsorbable bone fixation devices made from a high molecular weight of polymer of L(−)lactide. The polylactide bone fixation devices disclosed in the aforementioned patents can be used to fabricate plates and screws as well as intramedullary rods and pins which are used to secure the ends of fractured bones in proximity of each other so that they may properly heal.

European Patent Specification EP 0 321 176 B1, published Feb. 8, 1995, the disclosure of which is hereby incorporated by reference in its entirety, improved upon various known techniques for increasing the strength of thermoplastic materials in general (techniques such as heating and stretching thermoplastic sheets and tubes to impart molecular orientation and thereby increase strength, etc.); with particular focus on processes for increasing the tensile strength and flexural strength of thermoplastic materials used to fabricate bone fixation devices.

For background purposes, U.S. Pat. Nos. 3,248,463; 3,541,189; 3,630,824; 3,775,523; 4,157,235; 4,209,484; 4,413,110; and 4,577,998 (also cited in the incorporated reference) may be studied for their general teaching of techniques for strengthening thermoplastic materials.

Those skilled in the art will appreciate that the incorporated reference teaches the details of a process for specifically increasing the tensile strength of thermoplastic polymer materials such as, for example, polyesters and polyacrylics.

The disclosed process (disclosed in the incorporated reference by the inventor of the instant invention) was demonstrated as being particularly useful in the treating of polylactide (and similar polymers that are absorbable in an animal body), in a manner that provides significantly increased tensile strength and flexural strength for the absorbable pins, rods and screws formed from this polymer (polylactide).

One embodiment of a process disclosed in the incorporated reference includes the steps of melting an absorbable polymer by molding or extruding with little or no draw; and immediately cooling the polymer to a temperature below its glass transition temperature to cause nucleation and to form a "self-supporting member".

A "self-supporting member" is defined herein (as well as in the incorporated reference) as a member having sufficient structural rigidity that if the member is gripped or supported at one end thereof, the opposite end thereof will remain essentially in the same plane as the gripped or supported end. The term "self-supporting" is further intended to distinguish over flexible, or limber, members (such as a suture, monofilament fiber or the like) which, if gripped or supported at one end, will bend or droop such that the end of the member opposite the gripped or supported end will be substantially below the plane of the gripped or supported end.

Furthermore, according to the teachings of the incorporated reference, after the self-supporting member has been initially cooled, it is then reheated to a temperature above its glass transition temperature and below its melting temperature while applying tension to the self supporting member during the reheating step.

The member is then held under tension until it cools to room temperature. The application of tension is discontinued after the self-supporting member has cooled to permit the self-supporting member to relax.

By processing the polymer in this manner, tensile strength increases of up to 800 percent were achieved.

The incorporated reference also teaches a self-supporting high-strength member obtainable by the above process; and processes in which the aforementioned self-supporting high strength member is used for the manufacture of a bone fixation device (both bioabsorbable and non-bioabsorbable devices).

It should be noted that the processes taught in the incorporated reference contemplate that bone fixation devices may be formed either by a continuous process, e.g., extrusion; or by an intermittent process, e.g., injection molding.

As will be readily appreciated by those skilled in the art, bone fixation devices formed by a process that includes an extrusion step would have a substantially uniform initial cross-sectional shape; whereas, bone fixation devices formed by a process that includes a molding step could have a nonuniform shape as is explained by way of example in the incorporated reference.

Despite the advances in the art typified by the strengthening processes taught in the incorporated reference, it has been determined that the overall strength of the bone fixation devices (in particular bioabsorbable screws, such as the ones made by injection molding of the alpha-Hydroxyl polyesters, i.e. polylactic acid, polyglycolic acid etc.), when measured in terms of a given device's pullout strength, tensile modulus, shear strength and breaking torque strength, are too low to be of practical use in many areas of orthopaedic surgery.

Problems experienced which limit practical use of the aforementioned devices (in particular, screws) include their tendency to break either during insertion or break during use (but before bone healing is achieved), due to axial loading or shear loading; and their tendency to fail in the torsion mode (with layers of a screw separating from one another).

Accordingly, it would be desirable to provide processes for forming high strength thermoplastic polymer bone fixation devices (such as bone fixation screws) which exhibit improved pullout strength, tensile modulus, shear strength and breaking torque strength; particularly when compared with devices fabricated utilizing prior art techniques such as those described hereinabove.

Furthermore, it would be desirable to provide processes for forming both bioabsorbable and/or non-bioabsorbable versions of the aforementioned high strength thermoplastic polymer bone fixation devices.

Still further, it would be desirable to provide bone fixation devices that are products of the aforementioned processes and which are particularly well suited for use in orthopedic surgery.

More specifically, it would be desirable to provide bone fixation devices (in particular, bone fixation screws) that do not have a tendency to break (either during insertion or during use), due to axial or shear loading.

Further yet, it would be desirable to provide bone fixation devices (such as screws), that are suitable for use in orthopedic surgery and which in addition to not having the tendency to break during insertion and/or use, may be formed using a variety of bioabsorbable and/or non-bioabsorbable thermoplastic polymer materials to meet various application needs and demands.

SUMMARY OF THE INVENTION

In view of the foregoing, it is a general object of the present invention to provide processes for improving the strength of both bioabsorbable and non-bioabsorbable thermoplastic polymer bone fixation devices such as bone fixation screws.

More particularly, it is an object of the present invention to provide processes for improving the pullout strength, tensile modulus, shear strength and breaking torque strength of bone fixation devices (in particular bone fixation screws) produced by such processes; particularly when these characteristics are compared with corresponding characteristics for devices fabricated utilizing prior art techniques, such as those described hereinabove.

Furthermore, it is an object of the present invention to provide processes for forming bioabsorbable and non-bioabsorbable versions of the aforementioned high strength thermoplastic polymer bone fixation devices (including screws), utilizing process steps that can easily and cost effectively be run using, optionally and for example only, a continuous extrusion step as part of the process for forming molecularly oriented self-supporting inner core members used as part of the preferred process taught herein for fabricating high strength bone fixation devices.

Still further, it would be desirable to provide bone fixation devices (such as screws) that are products of the aforementioned processes and which are particularly well suited for use in orthopedic surgery.

More particularly, it would be desirable to provide bone fixation devices that do not have a tendency to break (either during insertion or during use), due to axial or shear loading; and to provide bone fixation devices that (depending on the need and application), may be formed using a a variety of bioabsorbable and/or non-bioabsorbable thermoplastic polymer materials.

According to one aspect of the invention, in order to increase the shear strength and/or the pull out strength of the desired devices (referred to hereinafter frequently as "screws" for the sake of convenience and illustration only), a new process has been developed.

According to a preferred embodiment of the invention, this process is a combination of an extrusion and an injection molding process that involves the use of three morphologically different forms of the same polymer (with different properties) and fabricating a bone fixation device from these different forms of the polymer. According to alternate embodiments of the invention the aforementioned processes could involve the use of different polymers and fabricating a bone fixation device from these different polymers.

The invention may best be appreciated by those skilled in the art by considering various aspects thereof to be set forth immediately hereinafter.

In particular, one aspect of the invention is directed to a process for fabricating a high strength bone fixation device, comprising the steps of: (a) forming a self-supporting highly molecularly oriented thermoplastic polymer inner core member (using, for example, the process set forth in detail in the incorporated reference); (b) forming an interfacial layer between the inner core member and a thermoplastic polymer outer layer for the device (which will be seen hereinafter as a means for improving the interfacial strength between the inner core member and the outer layer of the device); and (c) forming a thermoplastic polymer outer layer for the device, including the step of bonding the outer layer to the inner core member over the interfacial layer.

In the case where the bone fixation device is a screw (with the detailed description of the invention to be set forth hereinafter in the context of processes for forming screws and screw structures, for the sake of clarity and convenience only), the thermoplastic polymer outer layer includes, according to a preferred embodiment of the invention, screw threads and a head for the screw, which may be formed (for example) by an injection molding process after the inner core member is formed, cooled and layered with an interfacial layer of the type contemplated by the present invention (with suitable interfacial layers and processes for forming same to be described in detail hereinafter).

According to a preferred embodiment of the invention, the thermoplastic polymer used to form the aforementioned inner core member is melted by processing the polymer in an extruder to support continuous processing.

According to an alternate embodiment of the invention, the thermoplastic polymer may be melted using an injection molding process.

According to a further aspect of the invention, the step of forming the interfacial layer further comprises the step of creating a means for mechanically entangling the inner core member and the outer layer which, for example, may be created by forming at least one mechanical entanglement area along the length of the inner core member (or any other means for preventing slippage between the inner core member and the outer layer).

According to a preferred embodiment of the invention, the aforementioned step of creating a means for mechanically entangling the inner core member and the outer layer includes the step of forming at least one flattened section along the length of the inner core member by, for example, applying heat or ultrasonic energy at the desired location (or locations) where a flattened section is to be formed, after the inner core member itself has been formed and cooled.

In embodiments of the invention where a means for mechanically entangling the inner core member and the outer layer is created, the preferred process further calls for the step of actually mechanically entangling the outer layer and the inner core member utilizing the means for mechanically entangling (for example, imbedding the flattened area of the inner core member into the outer layer).

According to a yet another aspect of the invention, the step of forming the interfacial layer further comprises the step of coating the inner core member with means for improving the bonding between the inner core member and the outer layer. This step for forming the aforementioned interfacial layer may be performed in lieu of or in addition to any of the mechanical entanglement steps discussed hereinbefore.

According to a preferred embodiment of the invention, a means for improving the bonding between the inner core member and the outer layer is a solution that includes the same polymer used to form the outer layer and a solvent. The polymer in the solution is amorphous.

According to this aspect of the invention, the polymer in the solution, after being applied to (coating) the inner core member, forms a polymer bonding layer thereon; with the polymer applied in the solution being bonded first to the inner core member and then later to the outer layer (after evaporation of the solvent).

The polymer applied via the solution also preferably has a lower melting point than the polymer used to form the outer layer to, as will be discussed hereinafter, improve bonding efficiency and tend to minimize degradation of the outer layer applied via the aforementioned exemplary injection molding process.

According to a preferred embodiment of the invention, the bone fixation device formed utilizing the aforementioned processes is made using a bioabsorbable thermoplastic polymer, such as a polyester.

Alternate embodiments of the invention contemplate bone fixation devices formed using the aforementioned processes and thermoplastics that are non-bioabsorbable, such as where the non-bioabsorbable polymer is a polyacrylic.

Further aspects of the invention are directed to products of the aforementioned processes.

The invention features processes for forming bone fixation devices (such as bone fixation screws) that are bioabsorbable and exhibit high pull out strength and high shear strength; minimizing the tendency of such devices (in particular screws) from breaking either during insertion or use due to axial loading and/or shear loading.

The invention features processes for fabricating non-bioabsorbable devices with the same enhances strength features; products of all of the aforementioned processes which are in and of themselves new; and both processes and products thereof that realize all of the aforestated objects of the invention.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

As indicated hereinabove, the detailed description of the invention set forth hereinafter is presented in the context of processes for forming screws and screw structures per se. This presentation is not intended to limit the scope or spirit of the invention since, for example, other bone fixation devices such as bolts, rods having a head on one end, etc., may be fabricated using the teaching set forth herein.

Figure 1:
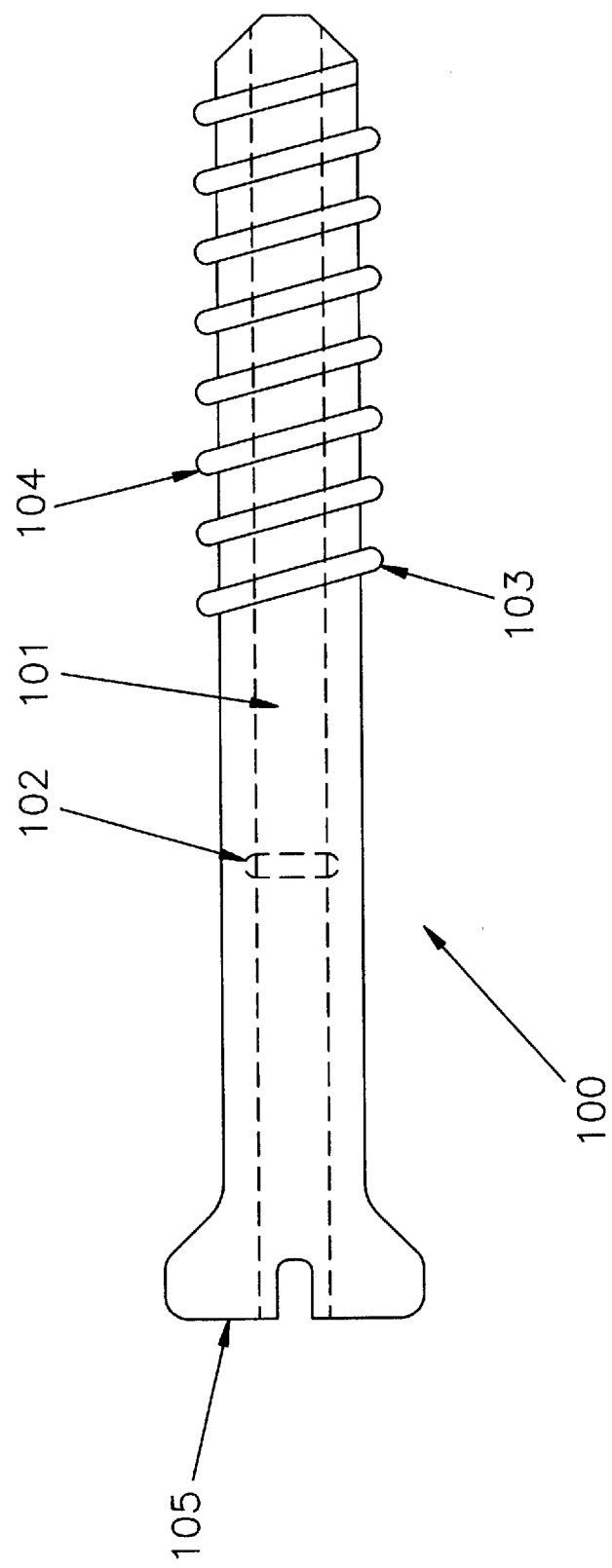
FIG. 1 depicts a side elevational view of an exemplary bone fixation screw of the type contemplated by a preferred embodiment of the invention.

Furthermore, the illustration and description of screw 100 in FIG. 1 is not meant to impose any limitation on the shape or size of any bone fixation device, or devices, or processes for fabricating same.

Figure 2:
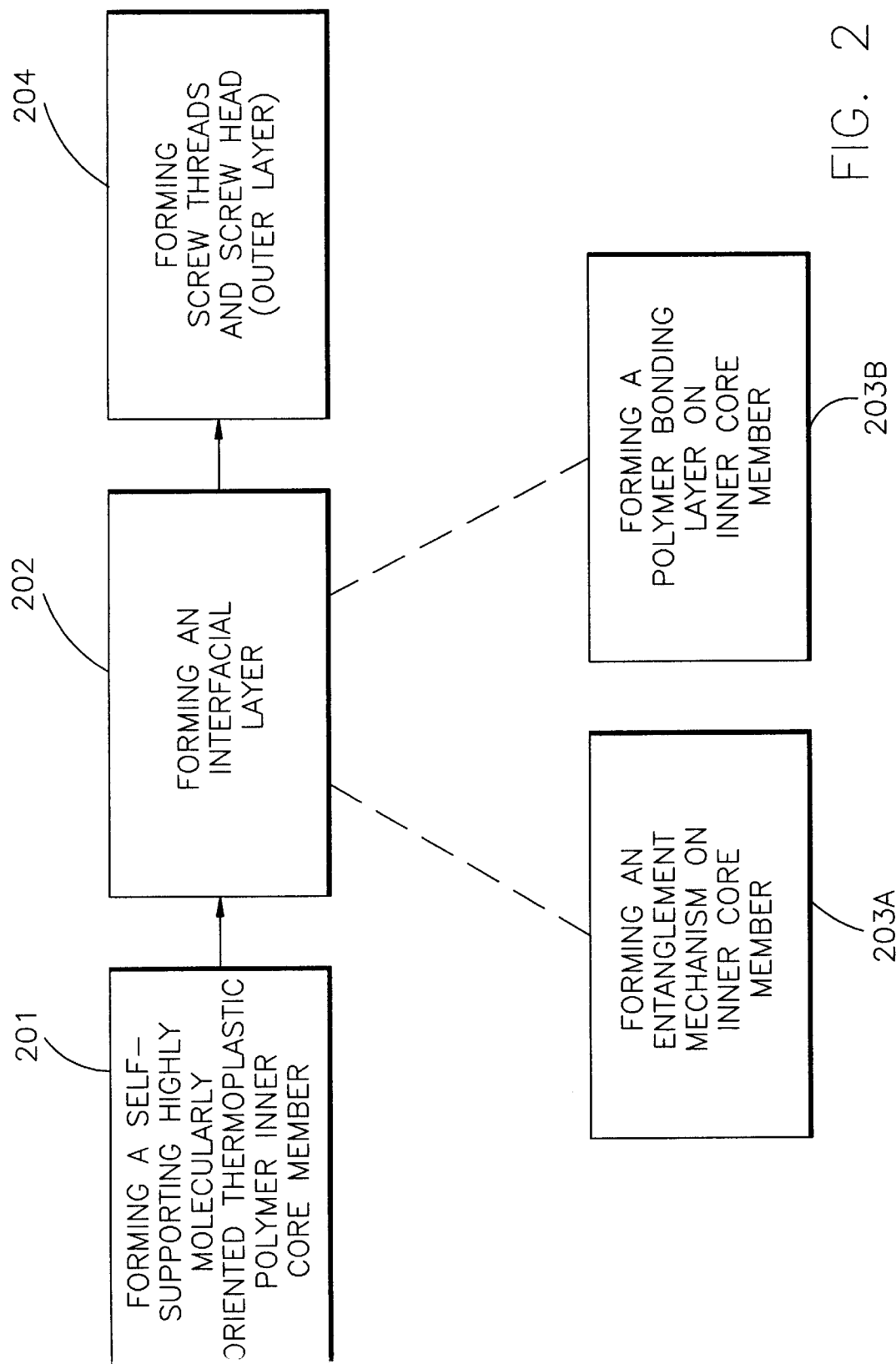
FIG. 2 depicts a process contemplated by a preferred embodiment of the invention for forming a screw of the type depicted in FIG. 1.

Accordingly, the following description of exemplary screw 100 shown in FIG. 1 and a suitable exemplary process for fabricating such a screw, described hereinafter in detail with reference to FIG. 2, is adopted for the sake of clarity and convenience only. It is intended that the scope of the invention only be limited by the claims appended hereto.

As indicated hereinabove, experiments conducted to evaluate the strength of bioabsorbable screws, such as ones made by injection molding of the alpha-Hydroxyl polyesters, i.e. polylactic acid, polyglycolic acid etc., indicated that screws possess insufficient strength to be of practical use in most areas of orthopaedic surgery. The problem with these screws is that they break either during insertion or during use (but before bone healing is achieved) due to axial loading or shear loading.

In order to increase the shear strength and/or the pull out strength of the screws it has been discovered, as indicated hereinbefore, that it is advantageous to use three morphologically different forms (components) of the same polymer (with the "same" polymer being preferred; but not a requirement to practice the invention), with different properties; and fabricating a screw from these.

An example of these three components may be seen with reference to FIG. 1 which, as indicated hereinabove, depicts a side elevational view of an exemplary bone fixation screw (screw 100) of the type contemplated by a preferred embodiment of the invention.

As will be demonstrated hereinafter with reference to FIG. 2, such a screw may be formed by utilizing the processes described hereinafter.

FIG. 1 shows a screw 100 having: (1) an inner core member 101; (2) an interfacial layer 102 between inner core 101 and an outermost layer; and (3) an outermost (outer) layer 103, each of the aforementioned layers to be described in greater detail immediately hereinafter.

In particular, inner core member 101 of screw 100 is intended to represent a highly molecularly oriented pin or rod of the type that may be manufactured utilizing the processes set forth in the incorporated reference.

According to a preferred embodiment of the invention, an extrusion process of the type described in the incorporated reference may be used to continuously and efficiently melt thermoplastic polymer as part of the process for forming a pin or rod that may serve as inner core member 101. Alternatively, an injection molding process (also described in the incorporated reference) may be used to form the pin or rod that can serve as inner core member 101.

Although described in detail in the incorporated reference, a suitable process for forming a highly molecularly oriented self-supporting rod (suitable for use as inner core member 101), will be set forth hereinafter for the sake of completeness.

In particular, a suitable (but not exclusive) process for forming inner core member 101 includes the steps of: (a) providing a thermoplastic polymer; (b) melting the thermoplastic polymer (by, for example, the previously referred to extrusion or injection molding process); (c) cooling the thermoplastic polymer to a temperature below its glass transition temperature to cause nucleation and to form a self-supporting member; (d) reheating the self-supporting member to a temperature above the glass transition temperature of the thermoplastic polymer, but below its melting temperature; (e) applying tension to the self-supporting member during the reheating step; (f) cooling the reheated self-supporting member while maintaining the tension applied thereto; and (g) discontinuing the application of tension after the self-supporting member has cooled to permit the self supporting member to relax.

An inner core formed in the above fashion will be partially crystalline and will impart high pull out strength and high shear strength to the screw (screw 100) being formed in accordance with the teachings of this invention.

Next, attention is turned to the forming of an interfacial layer located between the aforementioned inner core member 101 and outer layer 103, an example of which is shown as interfacial layer 102 in FIG. 1.

The interfacial layer contemplated by the invention is, in general, used to improve the bonding or load transfer between inner core member 101 and outer layer 103. According to preferred embodiments of the invention this objective may be accomplished by one or both of the following two methods (a) "mechanical entanglement", described in detail hereinafter with reference to FIG. 1; and/or (b) "stronger bonding", described in detail hereinafter as well.

"Mechanical entanglement" between inner core member 101 (again, preferentially formed via an extrusion process; but also capable of being formed by a molding process); and outer layer 103 (preferably formed via an injection molded process), increases the interfacial strength between these two components.

To achieve this the cylindrical inner core member 101 is shown to be flattened at one or more points along its length (specifically at 102 in FIG. 1). This may be accomplished by application of heat or ultrasonic energy to the inner core at the desired point or points.

The flat sections which form are imbedded in the injection molded polymer used to form outer layer 103, thus preventing the slippage that would otherwise occur between inner core member 101 and the outermost (outer) injection molded layer, 103.

As indicated hereinabove, an alternative process for providing the interfacial layer contemplated by the invention; an alternative which may be used in lieu of and/or in addition to the mechanical entanglement techniques discussed hereinabove, involves what has been referred to hereinbefore as a "stronger bonding" technique (or process).

According to a preferred embodiment of the invention, a means for improving the bonding between the inner core member and the outer layer is a solution that includes the same polymer used to form the outer layer and a solvent. The polymer in the solution is amorphous.

According to this aspect of the invention, polymer in the solution, after being applied to (coating) the inner core member, forms a polymer bonding layer thereon; with the polymer applied in the solution being bonded first to the inner core member and then later to the outer layer (after evaporation of the solvent).

The polymer applied via the solution also preferably has a lower melting point than the polymer used to form the outer layer. This aids in improving the bonding efficiency and tend to minimize degradation of the outer layer applied via the aforementioned exemplary injection molding process since (a) heat travelling from the outer layer 103 (being formed via the molding process) plasticizes the interfacial polymer bonding layer to strengthen the bond being formed and aid in bonding efficiency; and (b) the amount of heat required to melt the polymer bonding layer, due to its lower melting point, can be kept to a minimum thereby avoiding the undesirable degradation of outer layer 103 as it is being formed.

According to a preferred embodiment of the invention, the bone fixation device formed utilizing the aforementioned processes is made using a bioabsorbable thermoplastic polymer, such as a polyester.

Alternate embodiments of the invention contemplate bone fixation devices formed using the aforementioned processes and a non-bioabsorbable thermoplastic polymer.

In summary, the strong bonding between inner core member 101 and outer layer 103 may be achieved by bonding a layer of the same polymer which is amorphous and has lower melting point than the original polymer which is being injection molded. This can be achieved by coating a solution of the same polymer onto the core, evaporating off the solvent.

This type of interfacial layer, which is already bonded to inner core member 101 when outer layer 103 is being formed, bonds to the exemplary injection molded polymer outer layer 103 much better than core member 101 would bond to the exemplary injection molded polymer outer layer 103 (for the reasons set forth hereinbefore). Therefore, the presence of this interfacial layer increases the interfacial strength between inner core member 101 and outer layer 103.

Finally, with reference to FIG. 1, it should be noted that outer layer 103 functions (in the case of exemplary screw 100) to provide a least expensive way of forming screw threads 104 on inner core member 101, and forming head 105 for screw 100. This may be accomplished by injection molding into a mold the same polymer as used in the core forming; to form the screw threads (104) and the head of the screw (105).

Reference should now be made to FIG. 2 which, as indicated hereinbefore, depicts a process contemplated by a preferred embodiment of the invention for forming a screw of the type depicted in FIG. 1.

In particular, FIG. 2 call for process step 201 which is the step of fabricating (or forming) a self-supporting highly molecularly oriented thermoplastic polymer inner core member (like inner core member 101 shown in FIG. 1). Suitable methods for practicing this process step are, as indicated hereinbefore, completely taught in the incorporated EP 0 321 176 B1 reference.

Next, according to the present invention, an interfacial layer needs to be formed (shown as step 202 in FIG. 2) utilizing, for example, the mechanical entanglement and/or stronger bonding techniques taught hereinabove (or in fact, any other techniques which tend to increase the strength of the bone fixation device being formed to meet the objects of the present invention).

The use of either or both of the mechanical entanglement and/or stronger bonding techniques taught hereinabove is illustrated in FIG. 2 by either or both of process step 203*a* (forming an entanglement mechanism); and/or process step 203*b* (forming a polymer bonding layer) being practiced as part of step 202 (to which process steps 203*a* and 203*b* are shown coupled via dashed lines in FIG. 2).

Finally, FIG. 2 depicts the step of forming screw threads and a screw head (outer layer 103) to form the exemplary screw 100 depicted in FIG. 1. This is shown as process step 204 in FIG. 4, a variant of which (for example only) would include only forming a head via the outer layer, etc.

The invention and results achieved by utilizing the invention, will now be described with reference to a set of examples which constitute experiments conducted on various screws formed utilizing the teachings set forth herein.

It should be understood that any dimensions set forth hereinafter in the experiments are for purposes of example only, and are not meant to impose any limitation on the invention.

As indicated hereinbefore, certain embodiments of the present invention also specifically contemplate the bone fixation devices formed of a polymer that is absorbable in an animal body, such as the polylactide polymers disclosed in U.S. Pat. Nos. 4,539,981 and 4,550,449, the disclosures of which are hereby incorporated herein in their entireties by reference.

The melting point of such polylactide polymers varies depending on their thermal history. For example, if the polymer of the aforementioned patents is ground into a powder and fed directly into an extruder, or into the cavity of an injection molding machine, it will melt at approximately 210C. If the same polymer is melted and then formed into pellets, it will melt at a temperature of approximately 180C. The highest temperature in the extruder, or in the cavity of the injection molding machine, may be just slightly higher, e.g., about 10C higher, than the melting point of the polymer to avoid any degradation of the polymer.

Reference should now be made to the follow examples to appreciate the results achieved by practicing the invention described herein.

EXAMPLE 1

This example was undertaken to fabricate a control screw against which to evaluate screws made according to the teachings of the invention.

In particular, Example 1 illustrates the process of fabricating a screw without any inserts, thus it is the control screw. In Example 1, Poly-(L-lactide) was injection molded to make screws having a 5.2 mm. major diameter; a 3.2 mm. minor diameter; and a 52 mm. length.

The injection molding conditions were standard conditions for this polymer, with nozzle temperature of 220° C. The mold used was a standard mold.

Screws formed in the aforementioned manner were tested for Pullout Strength, Shear Strength, and for Breaking Torque Strength. For the first two tests an Instron Model 4505 was used. For the torque test an Electrotork, electronic torque measurement instrument from Snap-On Corporation was used.

The following results were obtained:

|  | MEAN | STD |
|---|---|---|
| Pullout Strength, N. | 529 | 96 |
| Tensile Modulus, Mpa | 1577 | 53 |
| Shear Strength, Mpa | 52.2 | 5.2 |
| Breaking Torque, in-lbs | 4.26 | 0.17 |

EXAMPLE 2

This example illustrates the use of the inner core member without the interfacial layer or entanglement areas. These screws were molded under the same conditions as those in Example 1; but a 2.0 mm diameter highly oriented pin made from the same polymer was placed into the center of the screw cavity in the mold and held there longitudinally during the injection molding of the thread around it.

The following results were obtained:

|  | MEAN | STD |
|---|---|---|
| Pullout Strength, N. | 522 | 84 |
| Tensile Modulus, Mpa | 1999 | 61 |
| Shear Strength, Mpa | 74.6 | 12.85 |
| Breaking Torque, in-lbs | 3.37 | 0.87 |

EXAMPLE 3

This example illustrates the use of a core insert with one flat entanglement area, everything else being the same as Example-2.

The following results were obtained:

|  | MEAN | STD |
|---|---|---|
| Pullout Strength, N. | 665 | 96 |
| Tensile Modulus, Mpa | 1998 | 111 |
| Shear Strength, Mpa | 97.9 | 5.5 |
| Breaking Torque, in-lbs | 3.59 | 0.62 |

EXAMPLE 4

This example illustrates the incorporation of the interfacial layer to increase the bonding strength between the inner core and the outer layer of injection molded polymer (in addition to the use of one entanglement area as used in Example 3).

The inner core pin was identical to the ones used in previous examples and was coated with a 2% solution of polylactide which was previously injection molded. The solvent used was chloroform. After the coating was completed the pin was first dried in air then under vacuum until constant weight is obtained. This coated pin was then used in the special mold as the insert for the screw.

Following results were obtained:

|  | MEAN | STD |
|---|---|---|
| Pullout Strength, N. | 728 | 45 |
| Tensile Modulus, Mpa | 2021 | 67 |
| Shear Strength, Mpa | 105.6 | 8.6 |
| Breaking Torque, in-lbs | 4.58 | 0.76 |

Examples 2,3,4 show various degrees of improvements in the strength of the screws which have the highly oriented thermoplastic polymer inner core member in them; especially when the screw formed using this core is strengthened using the interfacial layer techniques (such as being bonded to the injection molded outer layer) taught herein.

What has been described in detail hereinabove are processes and products of processes for forming high strength internal bone fixation devices (such as bioabsorbable screws, etc.) which meet all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

For example, the mechanical entanglement techniques taught herein could be used to form mechanical entanglement area in the head of a screw instead of or in addition to mechanical entanglement areas formed along the length of the inner core member. The mechanical entanglement areas need not be flattened areas but could, for example, be some form of prominence emanating from (or incision into) the inner core member, suitable for entangling the outer layer when it is formed, etc.

The embodiments and examples set forth herein were presented in order to best explain the principles of the instant invention and its practical application to thereby enable others skilled in the art to best utilize the instant invention in various embodiments and with various modifications as are suited to the particular use contemplated.

In view of the above it is, therefore, to be understood that the claims appended hereto are intended to cover all such modifications and variations which fall within the true scope and spirit of the invention.

What is claimed is:

1. A process for fabricating a high strength bone fixation device, comprising the steps of:
   (a) forming a self-supporting highly molecularly oriented thermoplastic polymer inner core member;
   (b) forming an interfacial layer for improving interracial strength between said inner core member and a thermoplastic polymer outer layer for said device, said interfacial layer including at least one of (i) means for mechanically entangling said core member and said outer layer, and (ii) a polymeric bonding layer; and
   (c) forming said thermoplastic polymer outer layer for said device including A step of bonding said outer layer to said inner core member over said interfacial layer.

2. A process for fabricating a high strength bone fixation screw, comprising the steps of:
   (a) forming a self-supporting highly molecularly oriented thermoplastic polymer inner core member for said screw;
   (b) forming an interfacial layer for improving interfacial strength between said inner core member and a thermoplastic polymer outer layer for said screw, said interfacial layer including at least one of (i) means for mechanically entangling said core member and said outer layer, and (ii) a polymeric bonding layer; and
   (c) forming said thermoplastic polymer outer layer for said screw, including a step of bonding said outer layer to said inner core member over said interfacial layer, wherein said thermoplastic polymer outer layer includes screw threads and a head for the screw.

3. A process as set forth in claim 2 wherein said step of forming a self-supporting highly molecularly oriented thermoplastic polymer inner core member for said screw further comprises the steps of:
   (a) providing a thermoplastic polymer;
   (b) melting said thermoplastic polymer;
   (c) cooling said thermoplastic polymer to a temperature below its glass transition temperature to cause nucleation and to form a self-supporting member;
   (d) reheating said self-supporting member to a temperature above the glass transition temperature of said thermoplastic polymer, but below its melting temperature;
   (e) applying tension to the self-supporting member during said reheating step;
   (f) cooling the reheated self-supporting member while maintaining the tension applied thereto;
   and
   (g) discontinuing the application of tension after the self-supporting member has cooled to permit the self supporting member to relax.

4. A process as set forth in claim 3 wherein said thermoplastic polymer is melted by processing it in an extruder.

5. A process as set forth in claim 3 wherein said thermoplastic polymer is melted by processing it in an injection molder.

6. A process as set forth in claim 2 wherein said step of forming said interfacial layer further comprises the step of creating a means for mechanically entangling said inner core member and said outer layer.

7. A process as set forth in claim 6 wherein said step of creating further comprises the step of forming at least one mechanical entanglement area along the length of said inner core member.

8. A process as set forth in claim 6 wherein said step of creating further comprises the step of forming means for preventing slippage between said inner core member and said outer layer.

9. A process as set forth in claim 6 wherein said step of creating further comprises the step of forming at least one flattened section formed along the length of said inner core member.

10. A process as set forth in claim 9 wherein said at least one flattened section is imbedded in said outer layer.

11. A process as set forth in claim 9 wherein said step of forming at least one flattened section formed along the length of said inner core member is performed by the application of heat to said inner core at the desired location for a given flattened section.

12. A process as set forth in claim 9 wherein said step of forming at least one flattened section formed along the length of said inner core member is performed by the application of ultrasonic energy to said inner core at the desired location for a given flattened section.

13. A process as set forth in claim 6 further comprising the step of mechanically entangling said outer layer and said inner core member utilizing said means for mechanically entangling.

14. A process as set forth in claim 2 wherein said screw is formed utilizing a bioabsorbable polymer.

15. A process as set forth in claim 14 wherein said bioabsorbable polymer is a polyester.

16. A process as set forth in claim 2 wherein said screw is formed utilizing a non-bioabsorbable polymer.

17. A process as set forth in claim 16 wherein said non-bioabsorbable polymer is a polyacrylic.

* * * * *